(12) United States Patent
Godara et al.

(10) Patent No.: US 11,291,496 B2
(45) Date of Patent: Apr. 5, 2022

(54) METHODS OF TREATING THE SACROILIAC REGION OF A PATIENT'S BODY

(71) Applicant: Avent, Inc., Alpharetta, GA (US)

(72) Inventors: Neil Godara, Milton (CA); Taylor Hillier, Georgetown (CA)

(73) Assignee: Avent, Inc., Alpharetta, GA (US)

( * ) Notice: Subject to any disclaimer, the term of this patent is extended or adjusted under 35 U.S.C. 154(b) by 337 days.

(21) Appl. No.: 15/918,297

(22) Filed: Mar. 12, 2018

(65) Prior Publication Data

US 2018/0199988 A1 Jul. 19, 2018

Related U.S. Application Data

(60) Division of application No. 14/270,668, filed on May 6, 2014, now Pat. No. 9,949,789, which is a division of application No. 11/428,458, filed on Jul. 3, 2006, now abandoned, which is a continuation-in-part of application No. 11/381,783, filed on May 5, 2006, now abandoned, which is a continuation-in-part of
(Continued)

(51) Int. Cl.
*A61B 18/14* (2006.01)
*A61B 18/00* (2006.01)

(52) U.S. Cl.
CPC ...... *A61B 18/1477* (2013.01); *A61B 2018/00023* (2013.01); *A61B 2018/0044* (2013.01); *A61B 2018/00083* (2013.01); *A61B 2018/00339* (2013.01); *A61B 2018/00434* (2013.01); *A61B 2018/00702* (2013.01); *A61B 2018/00744* (2013.01); *A61B 2018/00791* (2013.01); *A61B 2018/00839* (2013.01); *A61B 2018/00875* (2013.01); *A61B 2018/143* (2013.01)

(58) Field of Classification Search
None
See application file for complete search history.

(56) References Cited

U.S. PATENT DOCUMENTS 4,041,931 A 8/1977 Elliott et al.
4,202,349 A 5/1980 Jones
(Continued)

FOREIGN PATENT DOCUMENTS

CA 1160932 1/1984
EP 0547772 A1 6/1993
(Continued)

OTHER PUBLICATIONS

Ferrante et al., "Radiofrequency Sacroiliac Joint Denervation for Sacroiliac Syndrome", 2001, Regional Anesthesia and Pain Medicine, 2001, vol. 26, No. 2, pp. 137-142 (Year: 2001).*
(Continued)

*Primary Examiner* — Ronald Hupczey, Jr.
(74) *Attorney, Agent, or Firm* — Meunier Carlin & Curfman LLC

(57) ABSTRACT

A method, system and apparatus are disclosed for performing an electrosurgical treatment procedure on a bodily tissue. An electrosurgical apparatus is described, the apparatus comprising one or more probes having insulated and conductive regions for creating lesions in bodily tissue. A method of delivering energy to a patient's body is described, including methods of treating sacro-iliac related pain using electrosurgical probes.

14 Claims, 5 Drawing Sheets

Related U.S. Application Data application No. 11/356,706, filed on Feb. 17, 2006, now Pat. No. 8,951,249, which is a continuation-in-part of application No. 11/280,604, filed on Nov. 15, 2005, now Pat. No. 7,819,869, and a continuation-in-part of application No. 11/105,524, filed on Apr. 14, 2005, now Pat. No. 7,294,127, and a continuation-in-part of application No. 11/105,490, filed on Apr. 14, 2005, now abandoned, and a continuation-in-part of application No. 11/105,527, filed on Apr. 14, 2005, now Pat. No. 8,882,755, which is a continuation-in-part of application No. 10/087,856, filed on Mar. 5, 2002, now Pat. No. 6,896,675, said application No. 11/105,490 is a continuation-in-part of application No. 10/087,856, said application No. 11/105,524 is a continuation-in-part of application No. 10/087,856.

(56) References Cited

U.S. PATENT DOCUMENTS

| | | |
|---|---|---|
| 4,257,429 A | 3/1981 | Dickhudt et al. |
| 4,419,095 A | 12/1983 | Nebergall et al. |
| 4,447,239 A | 5/1984 | Krutten |
| 4,548,027 A | 10/1985 | Reimels |
| 4,612,934 A | 9/1986 | Borkan |
| 4,657,024 A | 4/1987 | Coneys |
| 5,191,900 A | 3/1993 | Mishra |
| 5,209,749 A | 5/1993 | Buelna |
| 5,342,343 A | 8/1994 | Kitaoka et al. |
| 5,342,357 A | 8/1994 | Nardella |
| 5,397,338 A | 3/1995 | Grey et al. |
| 5,429,597 A | 7/1995 | DeMello et al. |
| 5,429,617 A | 7/1995 | Hammersmark et al. |
| 5,433,739 A | 7/1995 | Sluijter et al. |
| 5,545,193 A | 8/1996 | Fleischman et al. |
| 5,571,147 A | 11/1996 | Sluijter et al. |
| 5,688,267 A | 11/1997 | Panescu et al. |
| 5,693,043 A | 12/1997 | Kittrell et al. |
| 5,759,174 A | 6/1998 | Fischell et al. |
| 5,766,171 A | 6/1998 | Silvestrini |
| 5,776,092 A | 7/1998 | Farin et al. |
| 5,779,642 A | 7/1998 | Nightengale |
| 5,800,428 A | 9/1998 | Nelson et al. |
| 5,855,577 A | 1/1999 | Murphy-Chutorian et al. |
| 5,895,386 A | 4/1999 | Odell |
| 5,951,546 A | 9/1999 | Lorentzen |
| 6,002,964 A | 12/1999 | Feler et al. |
| 6,056,743 A | 5/2000 | Ellis et al. |
| 6,102,886 A | 8/2000 | Lundquist et al. |
| 6,104,957 A | 8/2000 | Alo et al. |
| 6,126,654 A | 10/2000 | Giba et al. |
| 6,129,726 A | 10/2000 | Edwards |
| 6,146,380 A | 11/2000 | Racz et al. |
| 6,176,857 B1 | 1/2001 | Ashley |
| 6,235,000 B1 | 5/2001 | Milo et al. |
| 6,251,104 B1 | 6/2001 | Kesten et al. |
| 6,277,112 B1 | 8/2001 | Underwood et al. |
| 6,280,441 B1 | 8/2001 | Ryan |
| 6,306,132 B1 | 10/2001 | Moorman et al. |
| 6,315,790 B1 | 11/2001 | Gerberding et al. |
| 6,355,033 B1 | 3/2002 | Moorman et al. |
| 6,379,349 B1 | 4/2002 | Müller et al. |
| 6,464,723 B1 | 10/2002 | Callol |
| 6,471,700 B1 | 10/2002 | Burbank et al. |
| 6,478,793 B1 | 11/2002 | Moorehead |
| 6,501,992 B1 | 12/2002 | Belden et al. |
| 6,562,033 B2 | 5/2003 | Shah et al. |
| 6,582,426 B2 | 6/2003 | Moorman et al. |
| 6,620,156 B1 | 9/2003 | Garito |
| 6,622,731 B2 | 9/2003 | Daniel et al. |
| 6,726,684 B1 | 4/2004 | Woloszko |
| 6,735,474 B1 | 5/2004 | Loeb et al. |
| 6,757,565 B2 | 6/2004 | Sharkey |
| 6,770,070 B1 | 8/2004 | Balbierz |
| 6,773,446 B1 | 8/2004 | Dwyer et al. |
| 6,780,181 B2 | 8/2004 | Kroll et al. |
| 6,847,849 B2 | 1/2005 | Mamo et al. |
| 6,893,421 B1 | 5/2005 | Larsen et al. |
| 6,902,526 B2 | 6/2005 | Katzman |
| 6,932,811 B2 | 8/2005 | Hooven |
| 6,966,902 B2 | 11/2005 | Tsugita et al. |
| 6,974,454 B2 | 12/2005 | Hooven |
| 7,077,842 B1 | 7/2006 | Cosman |
| 7,097,641 B1 | 8/2006 | Arless et al. |
| 7,175,631 B2 | 2/2007 | Wilson et al. |
| 7,462,178 B2 | 12/2008 | Woloszko et al. |
| 2001/0000041 A1 | 3/2001 | Selmon et al. |
| 2001/0027309 A1 | 10/2001 | Elsberry |
| 2001/0056280 A1 | 12/2001 | Underwood |
| 2002/0026127 A1 | 2/2002 | Balbierz |
| 2002/0032440 A1 | 3/2002 | Hooven |
| 2002/0049437 A1 | 4/2002 | Silvestrini |
| 2002/0072739 A1 | 6/2002 | Lee |
| 2002/0091384 A1 | 7/2002 | Godinho de Queiroz e Melo |
| 2002/0103484 A1 | 8/2002 | Hooven |
| 2002/0120260 A1 | 8/2002 | Morris et al. |
| 2002/0147485 A1 | 10/2002 | Mamo et al. |
| 2002/0193781 A1 | 12/2002 | Loeb |
| 2003/0014047 A1 | 1/2003 | Woloszko |
| 2003/0015707 A1 | 1/2003 | Bosco |
| 2003/0023239 A1 | 1/2003 | Burbank et al. |
| 2003/0032936 A1 | 2/2003 | Lederman |
| 2003/0040742 A1 | 2/2003 | Underwood |
| 2003/0093007 A1 | 5/2003 | Wood |
| 2003/0100895 A1 | 5/2003 | Simpson et al. |
| 2003/0109870 A1 | 6/2003 | Lee |
| 2003/0120195 A1 | 6/2003 | Milo et al. |
| 2003/0125729 A1 | 7/2003 | Hooven |
| 2003/0153906 A1 | 8/2003 | Sharkey |
| 2003/0158545 A1 | 8/2003 | Hovda et al. |
| 2003/0212394 A1 | 11/2003 | Pearson et al. |
| 2003/0212395 A1 | 11/2003 | Woloszko |
| 2003/0233125 A1 | 12/2003 | Kaplan et al. |
| 2004/0054366 A1 | 3/2004 | Davison et al. |
| 2004/0082942 A1 | 4/2004 | Katzman |
| 2004/0106891 A1 | 6/2004 | Langan et al. |
| 2004/0187875 A1 | 9/2004 | He et al. |
| 2004/0199161 A1 | 10/2004 | Truckai et al. |
| 2004/0215287 A1 | 10/2004 | Swoyer et al. |
| 2004/0249373 A1 | 12/2004 | Gronemeyer et al. |
| 2004/0267203 A1 | 12/2004 | Potter et al. |
| 2004/0267254 A1 | 12/2004 | Manzo |
| 2005/0033372 A1 | 2/2005 | Gerber et al. |
| 2005/0049570 A1 | 3/2005 | Chin et al. |
| 2005/0085806 A1 | 4/2005 | Auge, II et al. |
| 2005/0096718 A1 | 5/2005 | Gerber et al. |
| 2005/0177209 A1 | 8/2005 | Leung et al. |
| 2005/0177211 A1 | 8/2005 | Leung et al. |
| 2005/0187542 A1 | 8/2005 | Auge |
| 2005/0240238 A1 | 10/2005 | Mamo et al. |
| 2006/0020297 A1 | 1/2006 | Gerber et al. |
| 2006/0025763 A1 | 2/2006 | Nelson et al. |
| 2007/0255370 A1 | 11/2007 | Bonde et al. |
| 2008/0200972 A1 | 8/2008 | Rittman et al. |

FOREIGN PATENT DOCUMENTS

| | | |
|---|---|---|
| EP | 0642800 A1 | 3/1995 |
| EP | 0651661 B1 | 6/2000 |
| EP | 0865768 A1 | 2/2003 |
| EP | 1344497 A1 | 9/2003 |
| WO | WO 81/03272 | 11/1981 |
| WO | WO 94/02077 | 2/1994 |
| WO | WO 1994/009560 A1 | 4/1994 |
| WO | WO 1994/022384 A1 | 10/1994 |
| WO | WO 1994/024948 A1 | 11/1994 |
| WO | WO 95/10320 | 4/1995 |
| WO | WO 1995/010318 | 4/1995 |
| WO | WO 1995/010327 A1 | 4/1995 |
| WO | WO 1995/021578 A1 | 8/1995 |
| WO | WO 1996/039967 A1 | 12/1996 |
| WO | WO 1997/006739 A2 | 2/1997 |
| WO | WO 1997/006855 A2 | 2/1997 |

(56) References Cited

FOREIGN PATENT DOCUMENTS

| | | |
|---|---|---|
| WO | WO 1997/024074 A1 | 7/1997 |
| WO | WO 98/19613 | 5/1998 |
| WO | WO 1998/019613 A1 | 5/1998 |
| WO | WO 1998/027879 A1 | 7/1998 |
| WO | WO 1998/031290 A1 | 7/1998 |
| WO | WO 1998/058747 A1 | 12/1998 |
| WO | WO 1999/042037 A1 | 8/1999 |
| WO | WO 1999/043263 | 9/1999 |
| WO | WO 1999/048548 | 9/1999 |
| WO | WO 2001/045579 | 6/2001 |
| WO | WO 2001/067975 A3 | 9/2001 |
| WO | WO 2001/070114 | 9/2001 |
| WO | WO 2001/074251 A3 | 10/2001 |
| WO | WO 2001/080724 A3 | 11/2001 |
| WO | WO 2002/045609 A1 | 6/2002 |
| WO | WO 2003/037162 A1 | 5/2003 |
| WO | WO 2003/065917 A1 | 8/2003 |
| WO | WO 2003/103522 A1 | 12/2003 |

OTHER PUBLICATIONS

Robinson et al., "Sacro-Iliac Joint Sensory Block and Radiofrequency Ablation: Assessment of Bony Landmarks Relevant for Image-Guided Procedures", BioMed Research Internation, vol. 2016, pp. 1-7 (Year: 2016).*

International Search Report (PCT/CA2006/001163)—7 pages.

International Search Report (PCT/CA2006/000229)—4 pages.

Bogduk et al., "Technical Limitations to the Efficacy of Radiofrequency Neurotomy for Spinal Pain", Neurosurgery 20(4):529-535, 1987.

Lord et al., "Percutaneous Radiofrequency Neurotomy in the Treatment of Cervical Zygapophyseal Joint Pain: A Caution", Neurosurgery 36(4):732-739, 1995.

Lau et al., "The Surgical Anatomy of Lumbar Medial Branch Neurotomy (Facet Denervation)", Pain Medicine 5(3):289-298, 2004.

Lord et al., "Percutaneous Radio-Frequency Neurotomy for Chronic Cervical Zygapophyseal-Joint Pain", New England Journal of Medicine 335(23):1721-1726, 1996.

Hooten et al., "Radiofrequency Neurotomy for Low Back Pain: Evidence-Based Procedural Guidelines", Pain Medicine 6(2):129-138, 2005.

Dreyfuss et al., "Lumbar Radiofrequency Neurotomy for Chronic Zygapophyseal Joint Pain: A Pilot Study Using Dual Medial Branch Blocks", ISIS Scientific Newsletter 3(2):13-30, 1999.

Curatolo et al., "Re: Niemisto L., Kalso E., Malmivaara A., et al. Radiofrequency Denervation for Neck and Back Pain: A Systematic Review Within the Framework of the Cochrane Collaboration Back Review Group. Spine 2003, 28:1877-88", Spine 30(2):263-268, 2005.

Conaghan et al., "Sacral Nerve Stimulation can be Successful in Patients with Ultrasound Evidence of External Anal Sphincter Disruption", Diseases of the Colon & Rectum 38(8):1610-1614, Aug. 2005.

Fortin et al., "Sacroiliac Joint Innervation and Pain", Am J Orthop 28(12):687-90, Dec. 28, 1999.

Valleylab—RF Pain Management System, Sep. 16, 2004, http://www.valleylab.com/static/pain/products-generator.html.

Cohen et al., "Lateral Branch Blocks as a Treatment for Sacroiliac Joint Pain: A Pilot Study", 2003, Regional Anesthesia and Pain Medicine, vol. 28 No. 2, 113-119.

Ferrante et al., "Radiofrequency Sacroiliac Joint Denervation for Sacroiliac Syndrome", 2001, Regional Anesthesia and Pain Medicine, vol. 26 No. 2, 137-142.

Kline et al., "Radiofrequency Techniques in Clinical Practice", 2001, Interventional Pain Management, 243-293.

Buijs EJ, Kamphuis et, Groen GJ. "Radiofrequency treatment of sacrolliac joint-related pain aimed at the first three sacral dorsal rami: A minimal approach". Pain Clinic. 18(2):139-146, 2004.

Jiang J., Xiao L.Z., Zheng H.S., Zhu H.Q. "Comparison between radiofrequency coagulation plus small needle knife and single method in treatment of sacrolumbar pain". Chinese Journal of Clinical Rehabilitation. 7(20): 2844-2845, 2003.

Plancarte RS, Mayer-Rivera FJ. "Radiofrequency Procedures for Sacral and Pelvic Region Pain", Pain Practice. 2(3):248-249 (2002).

Fukui S, Nosaka S. "Succesful relief of hip joint pain by parcutanaous radiofrequency nerve thermocoagulation in a patient with contraindications for hip arthroplasty", J Anesth. 15(3):173-175 (2001).

Cohen SP, Foster A. "Pulsed radiofrequency as a treatment for groin pain and orchlaigia", Urology, 62(3):645 (2003).

Kawaguchi M, Hashizume K, Iwata T, Furuya H. "Percuntaneous radiofrequency lesioning of sensory brances of the obturator and femoral nerves for the treatment of hip joint pain". Reg Anesth Pain Med. 26(6):576-561 (2001).

Akatov OV, Dreval ON. "Percutaneous radiofrequency destruction of the obturator nerve for treatment of pain caused by coxarthrosis". Stereotact Funct Neurosurg. 89(1-4 Pt(2): 278-280 (1997).

Ferrante FM, Aranda M, Delaney LR, Kim PS, King LF, Mannes AJ, Mardini IA, Roche EA. "Radiofrequency sacroiliac joint denervation for sacroiliac syndrome". Reg Anesth Pain Med. 26(2): 137-142 (2001).

Goplani AF, Malik A, Simopolous T. "A novel technique for treating nonsurgical hip pain with radiofrequency lesioning of the sensory branches of the obturetor and femoral nerves: a case report". Archives of Physical Medicine and Rehabilitation. 84(9): E23 (2003).

Pino CA, Hoeft MA, Hofsess C, Rathmell JP. "Morphologic analysis of bipolar radiofrequency lesions: implications for treatment of the sacroiliac joint". Reg Anesth Pain med. 30(4):335-338 (2005).

Yin W, Willard F. Carreiro J, Dreyfuss P. "Sensory stimulation-guided sacroiliac joint radiofrequency neurotomy: technique based on neuroanatomy of the dorsal sacral plexus". Spine. 28(20):2419-2425 (2003).

Ahadian, FM. "Pulsed radiofrequency neurotomy: advances in pain medicine", Curr Pain Headache Rep. 8(1):34-40 (2004).

Gevargez A. Groenemeyer D. Schirp S, Braun M. "CT-guided percutaneous radiofrequency denervation of the sacroiliac joint". Eur Radiol. 12(6):1360-1365 (2002).

Anis N. Chawki N, Antoine K. "Use of radio-frequency ablation for the palliative treatment of sacral chordoma", AJNR. 25(9):1589-1591 (2004).

Conaghan P, Farouk R. "Sacral nerve stimulation can be successful in patients with ultrasound evidence of external anal sphincter disruption". Diseases of the Colon and Rectum. 48(8):1610-1614.

Kirsch DG, EBB DH. Hernandez AH, Tarbell NJ. "Proton radiotherapy for Hodgkin's disease in the sacrum". Lancet Oncology. 6(7):532-533 (2005).

Leng WW, Chancellor MB. "How sacral nerve stimulation neuromodulation works". Urol Clin North Am. 32(1):11-8 (2005).

Kirkham APS, Knight SL, Craggs MD, Casey ATM, Shah PJR, "Neuromodulation through sacral nerve roots 2 to 4 with a Finetech-Brindley sacral posterior and anterior root stimulator". Spincal Cord. 40(6):272-281 (2002).

Simon S. "Sacroiliac joint injection and low back pain". Intervention Pain Management. 535-539 (2001).

Kline MT, Yin W. "Radiofrequency techniques in clinical practice". Interventional Pain Management. 243-293 (2001).

Cole AJ, Dreyfuss P, Stratton SA. "The Sacroiliac Joint: A Functional Approach", Critical Reviews in Physical and Rehabilitation Medicine. 8(1&2):125-152 (1996).

Atlihan D, Tekdemir I, Ates Y, Elhan A. "Anatomy of the Anterior Sacroiliac Joint With Reference to Lumbosacral Nerves". Clinical Orthopaedics and Related Research. 376: 2360241 (2000).

Calvillo O, Skaribas I, Turnipseed J. "Anatomy and Pathophysiology of the Sacroiliac Joint". Current Review of Pain. 4:356-361 (2000).

Davies PW, Luthardt F, Statts PS. "Radiofrquency Treatment in the United States", Pain Practice 2(3): 192-194 (2002).

Ebraheim NA, Lu J, Biyani A, Yeasting RA. "Anatomic Considerations for Posterior Approach to the Sacroiliach Joint", Spine. 21(23): 2709-2712 (1996).

(56) References Cited

OTHER PUBLICATIONS

Fortin JD, Washington WJ, Falco FJE. "Three Pathways between the Sacroiliac Joint and Neural Structures". Am J Neruoradiol. 20:1429-1434 (1999).
Liguoro D, Viejo-Fuertes D, Midy D, Guerin J. "The Posterior Sacral Foramina: An Anatomical Study". J. Anat. 195:301-304 (1999).
Murata Y, Takahashi K, Yamagata M, Takahashi Y, Shimada Y, Moriya H. "Origin and pathway of sensory nerve fibers to the ventral and dorsal sides of the sacroiliac joint in rats", Journal of Orthopaedic Research. 19:379-383 (2001).
Prithvi Raj P, Erdine S. "The Current Status of the Practice of Radiofrequency in the World". Pain Practice. 2(3):176-179 (2002).
Slipman CW, Whyte WS, Chow DW, CHou L, Lenrow D, Ellen M. "Sacroiliac Joint Syndrome". Pain Physician. 4(2):143-152 (2001).
Van Zundert J, Raj P, Erdine S, van Kleef M. "Application of Radiofrequency Treatment in Practical Pain Management: State of the art". Pain Practica. 2(3):269-276 (2002).
Dreyfuss P, Rogers CJ. "Radiofrequency Neurotomy of the Zygapophyseal and Sacroiliac Joints". Pain Proc. 2 (Chapter 32): 395-420 (2000).
Deer, T. "Injections for the Diagnosis and Treatment of Spinal Pain". American Society of Anesthesiologists 32(Chapter 6):52-69 (2004).
Cohen, Steven P. "Sacroiliac Joint Pain: A Comprehensive Review of Anatomy, Diagnosis, and Treatment". Anesth Analg 2005;101:1440-53.

\* cited by examiner

METHODS OF TREATING THE SACROILIAC REGION OF A PATIENT'S BODY

REFERENCES TO PARENT AND CO-PENDING APPLICATIONS

The present application is a divisional application of U.S. Ser. No. 14/270,668, filed on May 6, 2014, which is a divisional application of U.S. patent application Ser. No. 11/428,458, filed Jul. 3, 2006, which is a continuation-in-part of co-pending U.S. patent application Ser. No. 11/381,783, filed May 5, 2006, which is a continuation-in-part of U.S. patent application Ser. No. 11/356,706 filed Feb. 17, 2006 (now U.S. Pat. No. 8,951,249), which is a continuation-in-part of U.S. patent application Ser. No. 11/280,604, filed Nov. 15, 2005 (now U.S. Pat. No. 7,819,869); and U.S. patent application Ser. Nos. 11/105,527, 11/105,490, and 11/105,524, all filed on Apr. 14, 2005, and which are all continuations-in-part of U.S. patent application Ser. No. 10/087,856 (now U.S. Pat. No. 6,896,675) filed on Mar. 5, 2002. In addition, this application claims the benefit of: U.S. provisional application No. 60/595,426, filed Jul. 4, 2005; U.S. provisional application No. 60/595,559, filed Jul. 14, 2005; U.S. provisional application No. 60/595,560, filed Jul. 14, 2005; U.S. provisional application No. 60/743,511 filed Mar. 16, 2006; and U.S. provisional application No. 60/743,663, filed Mar. 22, 2006. The aforementioned applications are all incorporated herein by reference in their entirety.

TECHNICAL FIELD

The invention relates to an apparatus for creating a lesion to treat tissue and a method of using the apparatus to treat a target site.

BACKGROUND OF THE ART

Ablation of nerves is a common practice in the treatment of pain, and is currently used to treat back pain in the disc and in the facet joint. Ablation involves the heating of a tissue by the application of energy, in order to create a lesion; it is theorised that the lesioning of nerves renders them unable to transmit neural signals, thus eliminating nociceptive sensations therefrom. One common method of ablation involves the application of electrical energy from an electrode. Monopolar apparatuses use a grounding pad and a single electrode (or a group of electrodes at the same potential), whereby the electrical field is concentrated around the electrode(s) to generate heat within the tissue. Bipolar or multipolar apparatuses also exist, whereby the electrical current passes substantially between the electrodes, allowing a lesion to be created around each and, depending on the voltage or power used, extending between the electrodes.

Recently, research has led to growing interest in pain emanating from the sacroiliac (SI) joint and the surrounding region. Pain associated with the SI joint and surrounding region—which has been referred to in the literature as sacroiliac syndrome, sacroiliac joint dysfunction or sacroiliac joint complex (SIJC) pain amongst other terms—will, for clarity, be referred to throughout this specification as sacroiliac joint syndrome (SIJS). Referring to FIG. 1, the SI joint 110 is the region of a patient's body located between the sacrum 100, a large bone at the base of the spine composed of five fused vertebrae, and the ilium 102 of the pelvis. SI joint 110 is a relatively immobile joint, serving to absorb shock during locomotion. The structure of the SI joint varies significantly between individuals but generally comprises an articular cartilaginous surface, a ligamentous aspect and, in most cases, one or more synovial recesses. Historically, it was believed that SI pain was referred, and that the joint itself was not innervated, however, it has recently become accepted that nerves do enter the joint. Though the specific pathways of innervation have not yet been elucidated, the nerves responsible for SI pain are thought to comprise, at least in part, nerves 106 emanating from the sacral dorsal plexus, the network of nerves on the posterior surface of the sacrum, extending from the posterior primary rami or sacral nerves 108 that exit the sacral foramina 107. Diagnostic criteria for SIJS include (1) pain in the region of the SI joint with possible radiation to the groin, medial buttocks, and posterior thigh, (2) reproduction of pain by physical examination techniques that stress the joint, (3) elimination of pain with intra-articular injection of local anesthetic and (4) an ostensibly morphologically normal joint without demonstrable pathognomonic radiographic abnormalities.

While mechanical support devices exist for the alleviation of pain, there is currently no standardized method or apparatus for the treatment of SIJS. Yin et al. (Sensory Stimulation-Guided Sacroiliac Joint Radiofrequency Neurotonomy: Technique based on Neuroanatomy of the Dorsal Sacral Plexus; (2003) SPINE, Vol. 28, No. 20, pp. 2419-2425, which is incorporated herein by reference) suggest treatment of SIJS by lesioning a single branch of a sacral nerve as it exits the sacral foramina. The procedure described by Yin et al. may require a relatively skilled user due to the approach involved. In addition, the procedure detailed therein is time consuming as it involves multiple steps of probe re-positioning and neural stimulation in order to locate a single symptomatic nerve branch.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1:
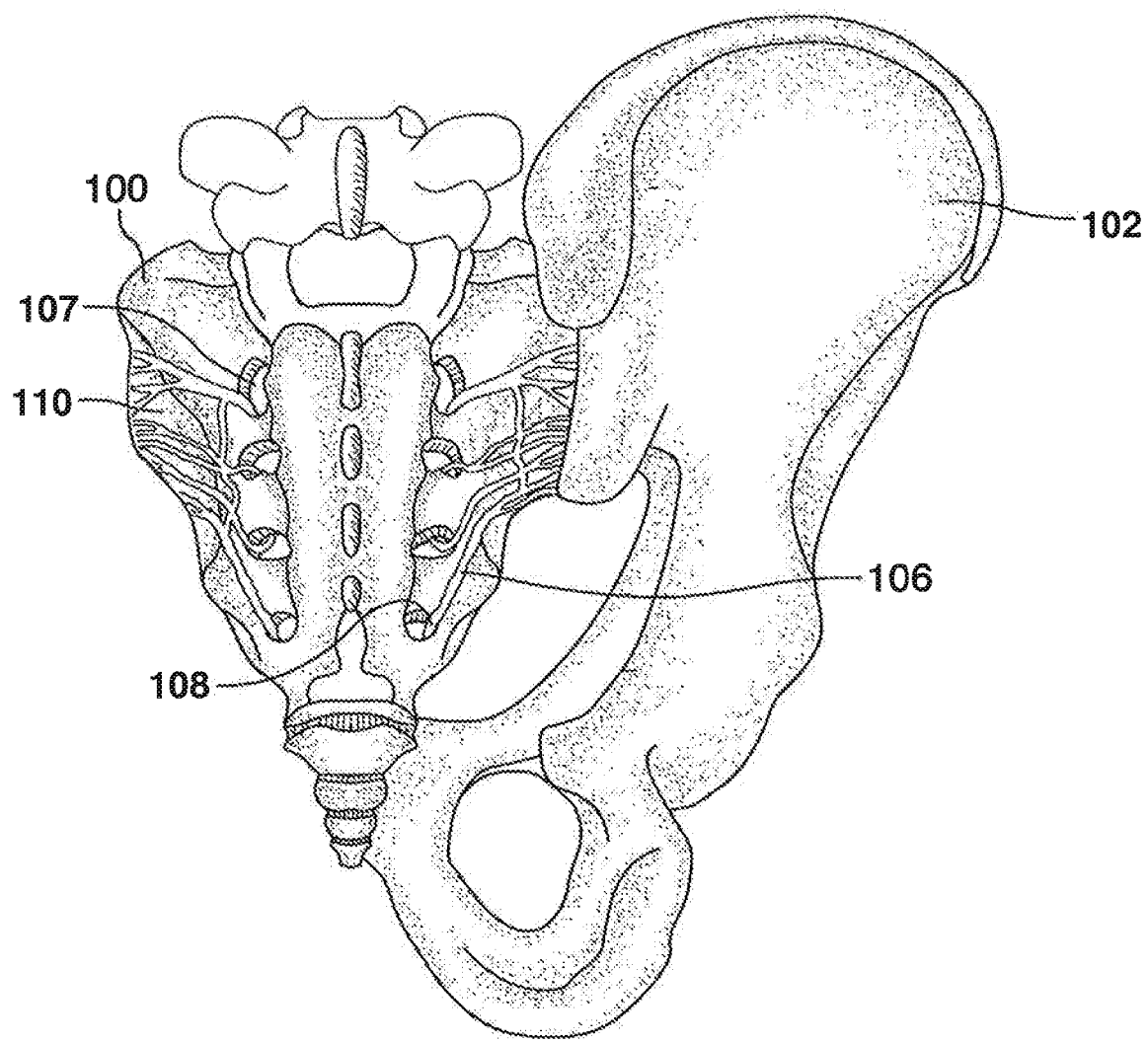
FIG. 1 shows a partial plan view of the sacro-iliac region of a human.

With specific reference now to the drawings in detail, it is stressed that the particulars shown are by way of example and for purposes of illustrative discussion of some embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In a broad aspect, the present invention includes an apparatus for delivering energy to a target site within the body and a method for using the apparatus to treat a target site, for example to treat pain due to SIJS.

Figure 2:
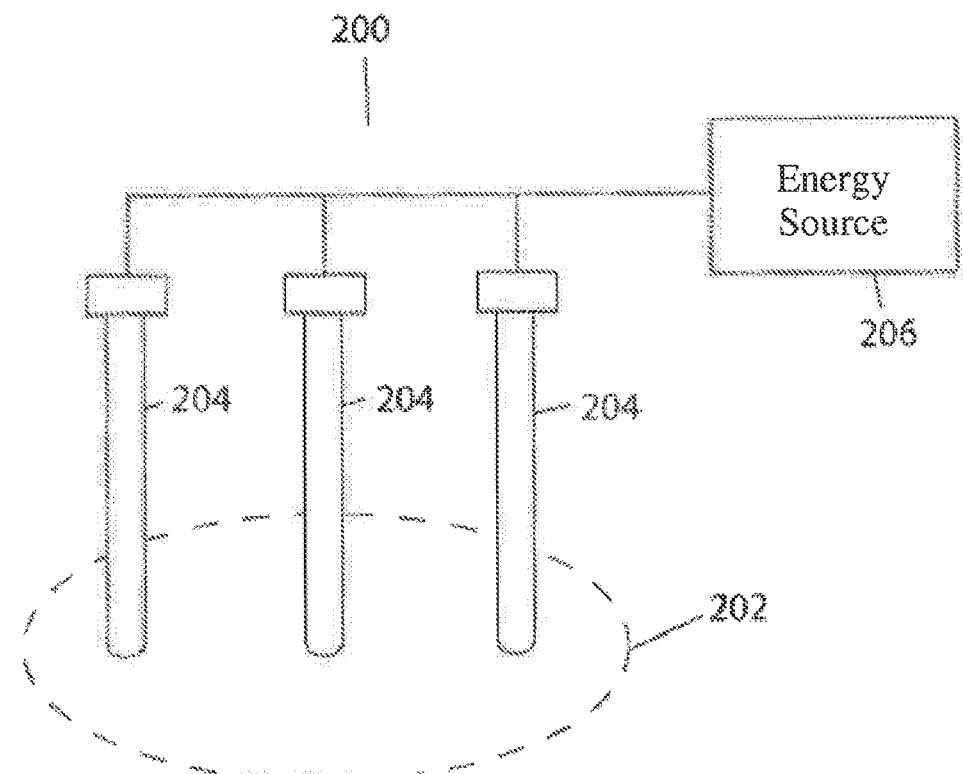
FIG. 2 shows a schematic block diagram of an embodiment of the apparatus of the present invention having 3 probes.

As shown in FIG. 2, an embodiment of a system 200 of the present invention for treating at least a portion of a target site 202 in a patient's body may comprise an embodiment of an apparatus of the present invention including at least one probe 204 and an energy source 206 for supplying energy to at least one of probes 204. In the context of the present invention, the term 'probe' is used to describe any elongate device that may be percutaneously inserted into a patient's body. These devices include but are not limited to catheters, cannulae and electrosurgical probes. For the sake of clarity, the term 'probe' is used throughout the specification to describe any such device.

Figure 3:
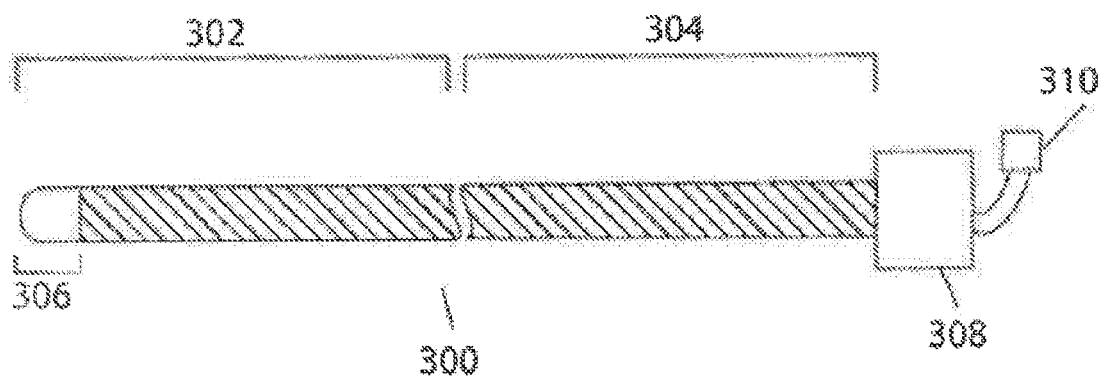
FIG. 3 is a side view of one embodiment of a probe of the present invention.

Some embodiments of a probe 204, as shown for example in FIG. 3, comprise an elongated shaft 300 with a distal region 302 and a proximal region 304. As used herein, the term 'proximal' is used to refer to a portion or region of a device or tissue that is located closer to the user of the device. 'Distal' refers to a portion or region of a device or tissue that is located closer to a treatment site and further away from the user. At least a portion 306 of distal region 302 is electrically conductive and exposed, and this conductive region 306 may be electrically coupled to energy source 206, thus allowing energy to be delivered to target site 202 via probe(s) 204. In some embodiments, the entire shaft 300 of probe 204 is made from a conductive material, which is overlain with an electrically insulating coating. In other embodiments, shaft 300 is made from an insulating material, with at least one conductive region 306 being affixed within or overtop of distal region 302 of shaft 300. In some embodiments, one or more probes 204 may be furnished with an insulating coating on one side of probe 204 at distal region 302, adjacent to conductive region 306 for directing current flow. Examples of such embodiments are provided in U.S. patent application Ser. No. 11/381,783, filed May 5, 2006, incorporated herein by reference.

Proximal region 304 of shaft 300 may comprise a handle 308 and one or more connector means 310 for connecting to energy source 206 or to another device such as a measuring device or a cooling means, for example a fluid delivery device. Connector means 310 may comprise one or more electrical cables or wires, one or more electrical connectors and/or one or more flexible tubes. Probe(s) 204 may have a variety of characteristics, for example: any of probes 204 may be straight or may have one or more bends anywhere along its length or may have a shape that is able to be changed, either manually or automatically. In the context of the present invention, the term 'bent' is used to describe any deviation from a longitudinal axis, whether it be a gradual or an abrupt deviation, and including all angles of deviation. Furthermore, distal regions 302 of probes 204 may be blunt, sharp, or pointed, or may take on any other shape; probes 204 may be solid in some embodiments but, in alternate embodiments, may be hollow and may define one or more channels or lumens. All probes 204 may have common characteristics, or may differ in terms of one or more characteristics; for example, the size of conductive region 306 may differ between the probes.

Probes 204 may be configured to deliver energy in a variety of configurations, for example, in a monopolar configuration, whereby all probes 204 are at the same electrical potential and energy may be delivered via probes 204 through a patient's body to a separate return electrode, or in a bipolar configuration, whereby energy flows substantially between two or more probes 204 or between two or more electrodes on one probe 204. If two or more probes 204 are used in a bipolar configuration any probe 204 may be an active or a return electrode. In further embodiments, probes 204 may be configured in a multipolar or multiphasic arrangement, whereby the probes 204 are configured such that the electrical potential and/or the phase of energy transmitted to at least two of the probes differs in such a way to cause energy to flow in a desired direction between the probes. Additionally, in order to direct the current to flow preferentially to a certain probe 204 or between a certain pair of probes 204, a resistance or impedance between energy source 206 and one or more probes 204, or between one or more probes 204 and a current sink (such as the circuit 'ground') or between two or more probes 204 may be varied. In other words, if it would be desirable to have current flow preferentially to a first probe, then the impedance between energy source 206 and any other probes may be increased so that current will flow preferentially to the first probe. Similarly, it may be desirable to have current flow between two or more specific probes. For example, a first and a second probe may be coupled to a first electrical pole while a third probe may be coupled to the opposite pole. Thus, current may flow between the third probe and either the first or second probe. If it would be desirable to have current flow between, for example, the third probe and the first probe, then an impedance between the second probe and circuit 'ground' may be increased so that current flows preferentially between the third and first probes. Thus, the flow of current to each of probes 204 may be independently adjustable by, for example, varying the impedance as mentioned above. In addition, flow of current to each probe 204 may or may not be concurrent. Thus, all probes 204 may be 'on' (i.e. transmitting or receiving current) at the same time or one or more probes 204 may be 'on' while other probes 204 are 'off' (i.e. not transmitting or receiving current). This may be implemented, for example, by using time-division multiplexing or various other switching means. Further details regarding the control of energy delivery to or between multiple probes are provided in U.S. patent application Ser. Nos. 11/105,527, 11/105,490, and 11/105,524, all filed on Apr. 14, 2005, all of which are incorporated herein by reference.

In embodiments having multiple probes 204, the probes 204 may be physically connected to form an attached probe assembly, for example, by having handles 308 of each probe attached to a common stage (not shown). Such a stage may be adjustable, so that the positions of probes 204 may be changed, relative to one another, for example, by being furnished with hinges or moveable components.

Figure 4A:
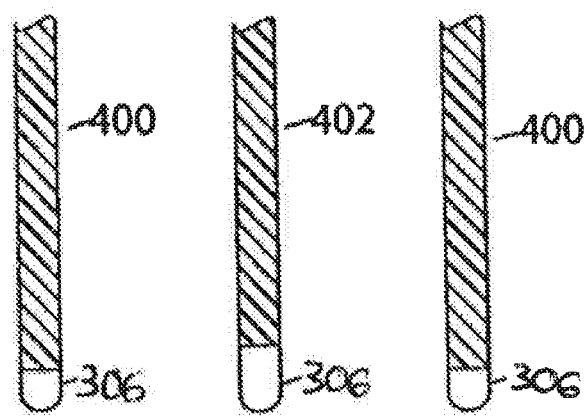
FIGS. 4A and 4B show side views of alternate embodiments of the present invention having 3 probes.

In one embodiment, as shown for example in FIG. 4A, the apparatus of the present invention comprises two probes 400, each measuring between about 60 mm to about 80 mm in length with a diameter between about 0.9 and about 1.3 mm, and a conductive region 306 at the distal tip about 1.5 to about 2.5 mm in length; and one probe 402 measuring between about 60 mm and about 80 mm in length with a diameter between about 0.9 and about 1.3 mm, and a conductive region 306 at the distal tip about 2 mm to about 4 mm in length. The probes may be arranged in a bipolar configuration, such that when energy is supplied to probes 400 from energy source 206, energy travels preferentially between each of probes 400 and probe 402, rather than between probes 400. Because probe 402 is receiving RF current from both probes 400, the conductive region of probe 402 may be larger, in order to maintain the current density around probe 402 at a level similar to that around each of probes 400. Depending on the distance between the probes, and on the properties of target site 202, one or more lesions may be created between each of probes 400 and probe 402.

Figure 4B:
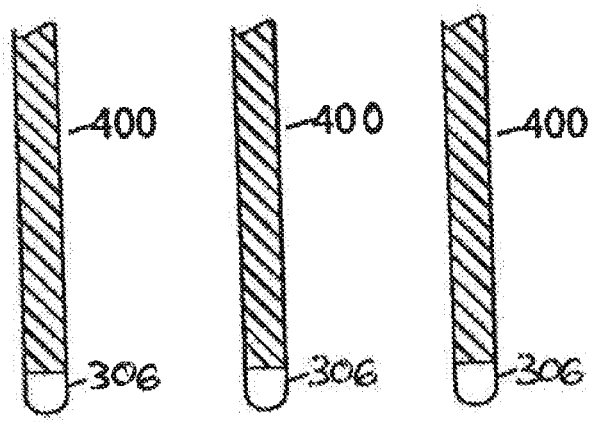

In another embodiment, shown in FIG. 4B, the apparatus of the present invention comprises three probes 400, each measuring between about 60 mm to about 80 mm in length with a diameter between about 0.9 and about 1.3 mm, and a conductive region 306 at the distal tip up to about 6.5 mm in length, more specifically about 4 mm in length. The probes may be configured in a monopolar configuration, such that when energy is supplied to probes 400 from energy source 206, the energy is concentrated around each of probes 400. Alternatively, the probes may be configured in a bipolar or multipolar configuration. Probes 400 may be separated by a distance such that energy delivery to one probe doesn't interfere with energy delivery to another probe in embodiments where energy is delivered to two or more probes substantially concurrently. For example, in embodiments wherein the three probes 400 are coupled to a stage, each probe 400 may be separated by a distance of about 5 times the diameter of the probes, i.e. about 4.5 to about 6.5 mm, for example about 5 mm. In further embodiments, the probes may be separated by a larger distance, for example about 5 to about 15 mm, more specifically about 10 mm. In embodiments of the apparatus comprising one or more cooled probes, the separation distance between probes 400 may be even greater, in order to account for the fact that the effective radius of energy delivery is increased due to the cooling as described further herein below. In such embodiments, the probes may be separated, for example, by a distance of about 10 to about 20 times the diameter of the probes, i.e. about 13 to about 26 mm, more specifically about 15 mm.

It will be appreciated that the specific measurements and dimensions referred to herein are by way of example only and are not intended to be limiting. Such measurements and dimensions can be selected by a person of ordinary skill in the art as appropriate for any particular application of the invention.

In some embodiments the conductive and exposed portion at the distal end of the probe may comprise only the distal face of the probe. For example, if the distal end is substantially rounded (as shown in FIG. 3), the distal hemisphere may remain exposed, while if the distal end is flat (not shown) the distal face or surface may remain exposed. Further details regarding such embodiments are provided in U.S. Provisional Patent Application 60/743,511 filed on Mar. 16, 2006, incorporated herein by reference. Such embodiments may be operable (with or without cooling) to form a lesion substantially distal to the tip of the probe, which may be desirable when employing a substantially perpendicular approach to a target site as disclosed herein below.

The probes may be configured to deliver high-frequency energy (such as radiofrequency (RF) energy) supplied by an energy source 206, for example a generator. One potential benefit of supplying high-frequency energy is that the high-frequency signal provides deeper tissue penetration than a typical DC or lower frequency signal. Depending on the voltage delivered to the target site 202 via the probes, the energy may generate sufficient heat in the tissue to cause lesions due to ablation or coagulation. In the context of the present invention, 'ablation' refers to raising the temperature of a tissue such that at least a portion of the tissue is coagulated and a lesion is formed within the tissue. A further benefit of using high-frequency energy is that it may allow for the creation of repeatable lesions. An additional benefit is that the frequency of the high-frequency energy is beyond the physiological range in the human body so that other organs, which use lower frequency signals, are not affected by this high-frequency signal. In alternate embodiments, other forms of energy may be delivered, including microwave energy, ultrasonic energy, thermal energy or optical energy (for example, via a laser).

Additionally, in some or all of the embodiments of the present invention, the apparatus may comprise one or more of: means for cooling the tissue adjacent a region of one or more probes 204 (for example, by the circulation of a cooling fluid through an internal lumen of the probe), means for changing the shape of at least a portion of one or more probes 204 (for example, using a spring or a guide wire or other means of actuation), means for facilitating the insertion of one or more probes 204 into a patient's body (for example, an introducer apparatus comprising a cannula and/or an obturator/stylet), means for visualizing one or more probes 204 once they have been inserted into a patient's body (for example, using a radiopaque marker in conjunction with fluoroscopic imaging or using some other imaging modalities), other tactile or visual markers and one or more additional functional elements for performing a procedure on the tissue (such as adding or removing material). As has been mentioned, probes 204 may be substantially rigid or may have various degrees of flexibility. Furthermore, one or more regions or segments of probes 204 may be manually or automatically deformable or steerable.

The use of cooling in conjunction with the delivery of energy to the target site may reduce the temperature of the tissue in the vicinity of the probe, where the most energy is delivered, allowing more energy to be delivered without causing an unwanted increase in local tissue temperature. Increasing the energy delivered to the tissue allows regions of the tissue further from the probe to reach a temperature at which a lesion can form, thus increasing the total maximum lesion volume. This may allow for probes to be placed further away from each other while maintaining sufficient temperatures between the probes to create a lesion between the probes. Further details regarding cooled probes are provided in U.S. patent application Ser. Nos. 11/105,527, 11/105,490, and 11/105,524, all filed on Apr. 14, 2005 and in U.S. Provisional Patent Application 60/595,559, filed Jul. 14, 2005; 60/595,560, filed Jul. 14, 2005; and 60/743,511, filed Mar. 16, 2006, all of which are incorporated herein by reference.

Embodiments of the apparatus of the present invention may further comprise a means for measuring one or more tissue properties, including but not limited to temperature and impedance. The apparatus may further comprise means of measuring pressure or other physical properties. The means of measuring temperature may comprise at least one thermocouple, thermistor or thermometer located anywhere along the length of one or more probes 204, or extending from one or more probes 204. The means of measuring pressure may comprise a lumen in fluid communication with an external environment as well as with a pressure transducer for recording pressure measurements. In other embodiments, the pressure measuring means may comprise a pressure transducer disposed at a desired location on the probe. Impedance may be monitored or measured by using a component of the apparatus as part of an impedance measuring circuit. For example, in embodiments of the present invention that employ more than one probe 204, the probes 204 used during the course of a treatment procedure may form part of the circuit of an electrical impedance meter, wherein energy may be transmitted between the probes 204 through a region of tissue, allowing a user to determine the impedance of said region of tissue. This feature may be useful to determine whether or not the impedance of the tissue lies within a 'normal' range—if the impedance of the tissue is found to be outside that range, it may be indicative of an injury or defect within the tissue. As mentioned above, a single probe 204 may also have an impedance measuring capability, for example to help determine the location of the probe 204 within a patient's body.

A means for measuring one of the properties mentioned above may optionally be used in conjunction with a means for controlling the operation of the apparatus based on said measured properties. For example, in one embodiment, at least one of probes 204 comprises at least one temperature sensor operatively connected to a controller, whereby the supply of energy to at least one probe 204 can be controlled by the controller based on the measurements received from the at least one temperature sensor. The controller may be in electrical communication with energy source 206, such that for example, if the measured temperature exceeds a specified upper threshold, the controller may perform a specified action, including but not limited to shutting down energy source 206 or decreasing the power delivered to probes 204 from energy source 206. In an alternate embodiment, the apparatus comprises impedance sensors which are connected to a controller and whereby the supply of energy may be controlled by the controller based on the measurements received from the impedance sensors. In additional embodiments, the operation of the apparatus may be modified in other ways, including but not limited to, terminating a treatment procedure, modifying the supply of a cooling means to one or more probes 204, or affecting a change in the conductivity or impedance of one or more probes 204. The operation of apparatus 200 may also be able to be manually controlled by a user, or may be automatically controlled based on other parameters, for example, based on a measurement of a property of a component of the apparatus itself, rather than a property of the tissue. Means of controlling the operation of the apparatus of the invention may optionally be configured to independently control one or more probes 204. As has been mentioned, current flow to any of probes 204 may be independently adjustable. In addition, the flow of cooling may be controlled independently to each probe 204. Thus, if one probe 204 is found to be at a higher temperature relative to other probes 204, flow of cooling to that probe 204 may be increased. Similarly, if one probe 204 is found to be at a lower temperature relative to other probes 204, flow of cooling to that probe 204 may be decreased.

Additionally, energy source 206 may be operable to supply stimulation energy to the body, whereby energy is delivered to target site 202 via one or more probes 204 at a frequency suitable for stimulating a muscular, sensory, or other response in the tissue. The effects of stimulation may be observed directly, such as visual observation of a muscle twitch or report of pain by the patient, or may be measured by an appropriate sensing means, for example an electromyogram (EMG) or somato-sensory evoked potential (SSEP) electrode, to measure the stimulation of muscle tissue. In accordance with embodiments of the present invention, stimulation of tissue may beneficially be practiced using the same apparatus configuration as is used to deliver energy for ablation/lesioning. In other words, the apparatus configuration used to ablate tissue may beneficially be used to stimulate tissue as well. For example, in one embodiment of the present invention as mentioned above, apparatus 200 is configured such that probes 400 and 402 form a pair of bipolar probe assemblies so that two lesions may form between each of probes 400 and probe 402. In such an embodiment, stimulation of tissue may be performed in a dual-bipolar fashion, wherein probes 400 and 402 form a pair of bipolar probe assemblies and wherein stimulation energy is delivered between each pair of bipolar assemblies. Alternatively, stimulation may be performed in a monopolar fashion, wherein stimulation energy is delivered between a probe and a dispersive electrode, for example a grounding pad, if the apparatus is configured to deliver treatment energy in such a manner. Thus, it may be desirable to perform a stimulation procedure using the same configuration to be applied in a treatment (i.e. lesioning/ablation) procedure in order to ensure the safety of the treatment procedure.

According to one embodiment of the present invention, probes 204 are fabricated from stainless steel. However, any biocompatible and conductive material, including but not limited to nickel-titanium alloys, may be used, depending on the desired structural properties of the probe. For example, in applications requiring a stiffer and stronger probe, stainless steel may be desirable, while nickel-titanium alloy may be used for applications requiring superior flexibility and/or shape memory. In alternate embodiments, as previously described, probes 204 may be manufactured from a non-conductive material including, but not limited to, polytetrafluoroethylene (PTFE), polyvinylchloride (PVC) or polyurethane, and a conductive region 206 may then be incorporated into or onto probes 204. The insulating material, used to insulate probes 204, may beneficially comprise PTFE, polyimide or paralene, but any insulating material, including but not limited to polyethylene terephthalate (PET), may be used and the invention is not limited in this regard. For example, in alternate embodiments, the insulating material may be semi-porous or partially conductive to allow for some leakage of current through the insulating material. It should be noted that different insulating materials can be used for different portions of probes 204 and the invention is not limited in this regard.

In one broad aspect, the present invention may provide a method for treating the sacroiliac region of a patient's body by delivering energy. In one embodiment, the method may comprise the steps of: inserting one or more probes into the sacroiliac region of a patient's body, wherein the one or more probes are inserted at an angle ranging between about 45.degree. to about 135.degree. relative to a face of a foramen to one or more target sites; and delivering energy from an energy source through the one or more probes to the target site(s). In a further broad aspect, the method of treating at least one target site in a sacroiliac region of a patient's body by delivering energy, the method comprises the steps of: inserting one or more probes into the sacroiliac region of a patient's body, wherein the one or more probes are inserted so as to be generally upstanding relative to a face of a foramen; and delivering energy from an energy source through the one or more probes to the at least one target site. The target site may for example be at least a portion of the sacroiliac region of a patient's body. In another embodiment, the method may comprise the steps of: inserting one or more probes into the sacroiliac region of a patient's body, wherein at least one of the one or more probes are positioned at least 1 cm lateral to a posterior sacral foramen; and delivering energy from an energy source through the one or more probes to at least one target site within the sacroiliac region of a patients body. In the context of the instant disclosure, the sacroiliac region refers to the region of the patient's body comprising the sacrum and ilium and their articulation (including the sacroiliac joints) or associated ligaments.

One general application of a method aspect of the present invention is for the creation of one or more lesions at a target treatment site in a patient's body, for example within the sacroiliac region. If a sufficient amount of energy (for example, about 1 to about 10 Watts and, in some embodiments, about 2 to about 5 Watts) is delivered to a region of tissue using the apparatus of the present invention, at a sufficient voltage (for example, about 10 to about 160 Volts and, in some embodiments, about 10 to about 65 Volts) to increase the heat of the tissue to or past the ablation temperature of the tissue (typically about 42.degree. C.), ablation will occur and one or more lesions will form. This ablation can include, but is not limited to, ablation of one or more of neural tissue, whose ablation can prevent the transmission of nociceptive sensation, structural or connective tissue, whose ablation can cause a contraction of collagen and a reduction in the volume of tissue, and vascular tissue, whose ablation may result in the disruption of nutrient supply to one or more neural structures. The specific geometry of the components of the apparatus, the positions and dimensions of the probes and the presence, absence and/or degree of cooling may affect the shape and size of any resulting lesions.

In accordance with one application of a method aspect of the present invention, a method is provided for the treatment of SIJS by creating one or more lesions to ablate nerves emanating from the posterior sacral foramina that innervate the SI region. This approach may be beneficial because it may allow for a treatment procedure that can effectively target neural tissue that innervates the SI joint without having to actually enter the joint itself. Furthermore, if a patient's pain is emanating from the SI ligaments, it may be beneficial to target the neural tissue before it reaches the ligaments in order to alleviate this pain. Generally, it may be beneficial to treat neural tissue as close to the nerve root as possible, in order to increase the effectiveness of the treatment procedure.

In one embodiment, it may be desired to treat one or more neural structures within a sacral neural crescent 506. The term 'sacral neural crescent' refers to an area lateral to each of the sacral foramina, through which the sacral nerves are believed to pass after exiting the foramina. On the dorsal right side of the sacrum, this window is from about 12 o'clock to about 6 o'clock in a clockwise direction, while on the dorsal left side of the sacrum the window is from about 6 o'clock to about 12 o'clock in a clockwise direction. Similar (but in the counter-clockwise direction) areas exist on the ventral side of the sacrum. The clock positions are referenced as if the foramen is viewed as a clock face, and the view is taken looking towards the sacrum. For reference, the 12 o'clock position of the clock face would be the most cephalad (towards the head) point of the foramen. Alternatively, the neural tissue may be treated at some position between a lateral edge of a sacral foramen and a margin of an SI joint. In some embodiments, the probe(s) used in this method aspect of the present invention may be operable to treat a plurality of neural structures without the need for one or more of removal of the probe(s), reinsertion of the probe(s) or repositioning of the probe(s). For example, at least two branches of the sacral nerves may be treated. These two branches may comprise two or more branches of the same sacral nerve or at least one lateral branch from one sacral nerve and at least one lateral branch from a different sacral nerve.

Thus, some embodiments of a method aspect of the present invention may generally comprise the steps of inserting one or more probes into a region of tissue adjacent one or more sacral foramina and delivering energy through the probe(s) in order to relieve symptoms of SIJS, wherein the energy may be delivered in order to ablate tissue. The energy may be delivered in a monopolar, bipolar, multipolar or multiphasic manner. When more than one probe is used, each of the probes may be independently controlled. For example, the temperature at the distal end of each of the probes may be monitored, and the power delivered to each of the probes may be adjusted based on the temperature of each of the probes. Two specific examples of such embodiments will be presently described.

Figure 5A:
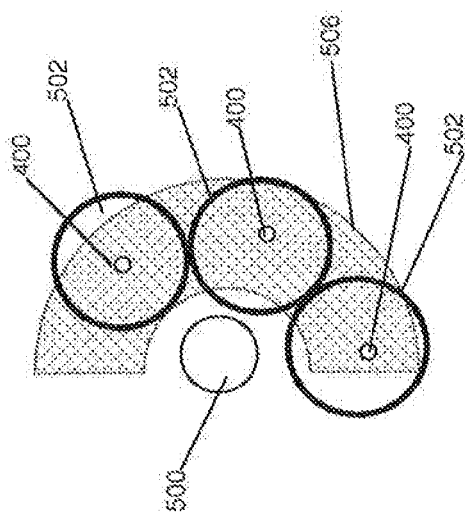
FIGS. 5A, 5B, 5C, and 5D are schematic top plan views illustrating embodiments of a method of the present invention.

In one specific embodiment of this aspect of the present invention shown in FIG. 5A, two probes 400 having conductive tips 306 of equal length and one probe 402 having a longer conductive tip are inserted lateral to a sacral foramen, more specifically, within a sacral neural crescent 506. In some embodiments, the probes may be positioned to be generally upstanding or substantially perpendicular relative to the circular face of foramen 500 (i.e. the surface of the sacrum or sacral plate), and in some embodiments the probes may be positioned such that at least a portion of the target site is generally distal to the distal ends of the one or more probes. For example, the shaft of the probes may be at an angle of between about 80.degree. to about 100.degree., relative to the circular face of foramen 500, or alternatively, in some embodiments, the angle between the probe shaft and the face of the foramen may be between about 60.degree. to about 120.degree., or in alternate embodiments, between about 45.degree. to about 135.degree., i.e. relative to the circular face of the foramen. The probes may be operable in a dual-bipolar configuration, whereby probes 400 lie at a first electric potential and probe 402 lies at a second electric potential such that current flows substantially between each probe 400 and probe 402. In other embodiments, an alternate number of probes may be used, for example five probes may be used, three of which may lie at a first electric potential, and two of which, alternating between the first three probes, may lie at a second electric potential, as shown in FIG. 5C. It will be appreciated that in other embodiments the angle between the probe shaft and the face of the foramen may vary from the ranges referenced above.

The step of inserting one or more probes adjacent one or more sacral foramina may comprise visualizing a foramen 500 adjacent to a target site, for example using fluoroscopic imaging, penetrating into the tissue overlaying the sacrum using one or more rigid introducer apparatuses or other insertional means, and inserting the probes through the insertional means. In embodiments using multiple probes that are coupled, for example to a stage or other probe assembly, as described above, the step of visualization may be followed by a step of adjusting the positions of the probes relative to the assembly prior to insertion of the probes. Thus, the probe(s) may be inserted substantially concurrently, for example by using a probe assembly to which the probes are coupled, or they may be inserted sequentially, for example one at a time. The probes may be inserted substantially perpendicularly to the circular face of the foramen, such that when visualizing the foramen using a fluoroscope or x-ray, visualization of the probes will be along the length of the probe shaft, in a "gun barrel" view; this angle of approach may potentially minimize tissue damage during insertion as a minimal amount of tissue will need to be penetrated, and may also aid in proper positioning of the probes. Penetration into the tissue may also be facilitated by the use of sharp or pointed probes, by the use of an obturator/stylet, by the insertion of a guide wire or by any other insertional means (i.e. means for insertion) and the invention is not limited in this regard. It should also be noted that the introducer(s) or other insertional means may be electrically and/or thermally insulated and they may be bent or straight. Furthermore, the length and diameter of the insertional means are not limited to specific values and any suitably sized introducer may be used. For clarity, the term introducer will be used throughout this specification and is intended to encompass any means for insertion that may facilitate entry of a probe into a specific site within the body of a patient. In such embodiments, these introducers may be capable of penetrating into a patient's body as well as penetrating through one or more of the ligaments of the sacroiliac region. In alternate embodiments, a probe may be positioned at the appropriate location within a patient's body without using any additional means to facilitate insertion.

Thus, in this embodiment of this aspect of the present invention, and with reference again to FIG. 5A, a method for treating SIJS may be practiced as follows: a patient is made to lie prone on an operating table or similar structure, and local anesthetic is provided in the vicinity of the sacrum. Prior to the insertion of the probe(s) or introducer(s), fluoroscopic imaging, including, in some embodiments, the injection of a radiopaque contrast agent, or other means may be used to visualize a patient's sacroiliac region in order to ascertain a desired approach for inserting the device(s) into the desired tissue. This may be particularly advantageous with respect to SIJS treatment procedures because the anatomical structures involved may vary significantly from patient to patient. In this embodiment, following visualization to align the plane of visualization and foramen 500 adjacent the treatment site, the probes may be inserted radially away from, for example lateral, caudal, or cranial to, the lateral edge of a foramen, for example about 6 to about 12 mm, more specifically about 10 mm from the lateral edge. Probe 402, with a relatively larger conductive region, may be placed lateral to the lateral edge of a foramen at approximately the 4 o'clock position when the foramen is viewed as a clock face. The two probes 400, with relatively smaller conductive regions, may be placed—one substantially cranial and one substantially caudal to probe 402—at approximately the 2 o'clock and 6 o'clock positions, for example about 6 to about 10 mm and, more specifically, about 8 mm from the lateral edge of the foramen. As used herein, the terms 'substantially cranial' and 'substantially caudal' may refer to any position cranial or caudal to a reference point, respectively, whether at the same lateral position or another lateral position. It should be noted that the aforementioned probe positions relate to a foramen on the right side of the sacrum when facing the posterior of the sacrum. For the left-sided foramina, the equivalent positions would be 8 o'clock for probe 402, and 10 o'clock and 6 o'clock for probes 400. Furthermore, depending on the specific anatomy of the patient and the desired lesion shape and location, the probes may be positioned at other locations, and the invention is not limited in this regard. For example, in some embodiments, the probes may be positioned at 1 o'clock, 3 o'clock, and 5 o'clock. In yet further embodiments, wherein an alternate number of probes are used, the probes may be placed at other locations. For example, as shown in FIG. 5C, if five probes are used, the probes may be placed at 12 o'clock, 2 o'clock, 3 o'clock, 4 o'clock, and 6'o'clock.

In one embodiment of this aspect of the present invention, three introducers are inserted into a patient's body from an approach that is substantially perpendicular to the surface of the target treatment site adjacent the foramen, such that a distal end of each introducer is positioned proximate to or adjacent the lateral edge of sacral foramen 500. In some embodiments, the distal ends of the introducers and/or probes are positioned substantially superficial to the sacral bony surface, such that, in particular embodiments, there are no ligaments or other connective tissue between the distal ends of the introducers and/or probes and the sacrum. In further embodiments, the distal ends of the introducers and/or the probes may be placed about 2 to about 6 mm away from the surface of the sacrum, for example about 4 mm away from the surface. For example, an introducer apparatus may be about 2 to about 6 mm longer than a probe such that, when a distal end of the introducer is placed adjacent to the surface of the sacrum, the distal end of a probe fully disposed within the introducer may be located about 2 to about 6 mm away from the surface. In other embodiments, various angles of approach and sites of entry may be used. Depending on the site of entry and the angle of approach that are chosen, the introducer may be either bent or straight. A bent introducer may take several forms and the invention is not limited in this regard. For example, it may be bent along a substantial portion of its length or it may have a bent tip, wherein the rest of the introducer may be straight. At this point, the position of one or more introducers may be verified using fluoroscopic imaging (or other imaging modalities) or other means, after which the probes may be inserted through a bore or lumen of each introducer. The probes may be positioned at an angle such that the target treatment site is visualized straight down the shaft of the probes, and the probes may appear in cross-section, as shown in FIG. 5. It should be noted that, in those embodiments that comprise a stylet to facilitate positioning of the probe, the stylet may be disposed within an introducer and may be removed from the introducer prior to insertion of the probe.

It is advisable, at this stage, to ascertain the location of one or more of the probes with respect to any sensory and/or motor nerves that may be located close to the conductive regions of the probes by stimulating the neural tissue at one or more frequencies and determining the effect of said stimulation, as has been described. As mentioned above, the stimulation of neural tissue may be performed in a bipolar manner, wherein energy passes between two or more probes, or in a monopolar manner, wherein energy passes between one or more probes and a dispersive return electrode. Using this step, it can be determined whether a target nerve or nerves has a function that would contraindicate its ablation or functional alteration. In this embodiment, the lack of a contraindication would lead to the step of delivering energy, whereas the presence of a contraindication would lead back to the step of inserting a probe or probes, whereby the step of inserting a probe or probes comprises modifying the position of a probe or probes within the body. Further details regarding stimulation of neural tissue are provided in U.S. patent application Ser. Nos. 11/105,527, 11/105,490, and 11/105,524, all filed on Apr. 14, 2005, and all previously incorporated herein by reference. In alternate embodiments, no stimulation is performed and a user may rely on his or her knowledge, for example of the anatomical features of this region of the patient's body, in order to determine whether or not to proceed with the treatment procedure.

At this point, energy may be delivered from energy source 206 via the probes to the target treatment site. Referring still to FIG. 5A, energy may be delivered in order to create a lesion lateral to foramen 500, within at least a portion of the sacral neural crescent 506, such that the lesion may, in some embodiments, encompass at least one sacral nerve exiting foramen 500 and/or one or more lateral branches of the at least one sacral nerve. For example, in embodiments utilizing bipolar RF, a "dog bone"-shaped lesion may form between each pair (400, 402) of bipolar probes, which may result in a lesion 502 as shown in FIG. 5A.

Figure 6:
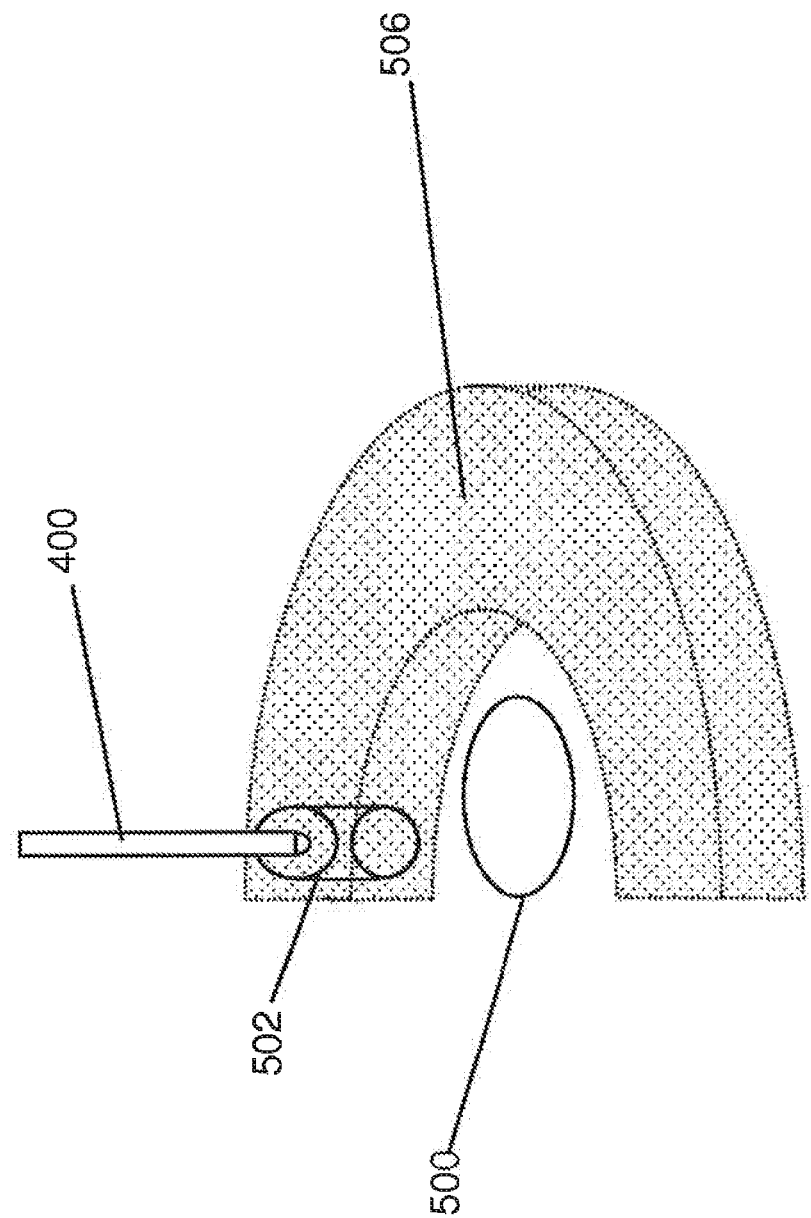
FIG. 6 is a perspective view showing one embodiment of a lesion located within a sacral neural crescent.

In some embodiments, for example as shown in FIG. 6, the lesion may have a height of about 1 mm to about 15 mm, for example about 8 mm to about 10 mm, in order to account for variability in the location of the nerves to be treated in the anterior-posterior plane of the patient's body. In some embodiments, the user may adjust a parameter of the treatment procedure in order to modify the height of the lesion, and thereby increase the size of the lesion. For example, in order to achieve the desired lesion height, the probe(s) may be withdrawn slightly from the patient's body, for example by about 2 mm to about 5 mm, and the step(s) of energy delivery may be repeated. These steps (i.e. withdrawing the probes and delivering energy) may be repeated until the desired lesion is formed. In some embodiments, any one or more of the probe(s) may comprise at least two electrodes wherein energy may be delivered between the electrodes in a bipolar manner. In such embodiments, lesion height or length may be increased relative to a monopolar probe due to the fact that energy will travel further along the length of the probe, between the electrodes. Alternatively, the probe(s) may have longer active tips in order to form a lesion of a desired height. In such embodiments, the probe(s) may be operable to create an elongated lesion, for example a strip lesion. For example, the probe(s) may comprise alternating regions of conductive and non-conductive surfaces, in order to create an elongate, substantially homogeneous lesion. Further details regarding such probes are provided in U.S. patent application Ser. No. 11/356,706 filed Feb. 17, 2006, incorporated herein by reference. In another embodiment, the probe(s) may be structured such that the length of the electrically exposed active tip may be adjustable; for example, the insulative coating may be structured, for example as a sheath, to slide back and forth on the shaft of the probe. By sliding the insulation proximally, the user may adjust the electrically exposed length of the active tip, thus effectively adjusting the height of the lesions that may be formed by the tip. In a further embodiment, the height of the lesion may be modified by adjusting an amount of cooling supplied to the probe. As is disclosed in U.S. Provisional Patent 60/743,511 (filed on Mar. 16, 2006), incorporated herein by reference, cooling a probe may allow for a lesion to form at a position located away from the probe. By supplying a high amount of cooling to the probe, a lesion will form substantially distally to and remote from the conductive region 306 of the probe. If the amount of cooling supplied to the probe is reduced, a lesion will form closer to the probe. Thus, by modifying the amount of cooling supplied to the probe, a lesion may form at various heights relative to the probe and the sacrum. As will be described below, energy delivery between the probes may be substantially concurrent or it may be sequential, depending, for example, on the number of probes used, the energy source 206 and the preferences of the user.

Following the step of energy delivery, if one or more of the probes are steerable, the tips of one or more of the probes may be maneuvered to a second location and energy may again be delivered to ablate the neural tissue at the second location. This may be repeated as many times as the user feels is necessary. If no probes are steerable, the insertion and positioning steps may be repeated so that one or more of the probes is removed and reinserted to a second position, at which point energy may be delivered again at this location. For example, in some embodiments, only two probes may be used, for example one probe 400 and one probe 402. In such embodiments, probes 400 and 402 may be placed adjacent to the foramen as indicated above, for example with probe 400 at the 6 o'clock position. After energy delivery has been completed at this position, probe 400 may be removed and reinserted into the 2 o'clock position, leaving probe 402 in place. The step of energy delivery may then be repeated. Once the user has determined that enough neural tissue has been ablated, the introducer and the probe may be removed from the body and the patient should be allowed to recover. It should be noted that in some embodiments, a step of re-inserting the probe(s) may not be required. For example, based on the specific anatomy of the patient, the user may determine, for example by using stimulation, that only a portion of the region surrounding the foramen needs to be ablated in order to, for example, relieve a patient's pain. In such an embodiment, the user may form a single lesion adjacent the foramen and substantially between two probes. It should be further noted that this description is intended to be exemplary only and that other embodiments are envisioned as well. In addition, this invention is not intended to be limited by the number and type of probes used in this and other embodiments.

Figure 5B:
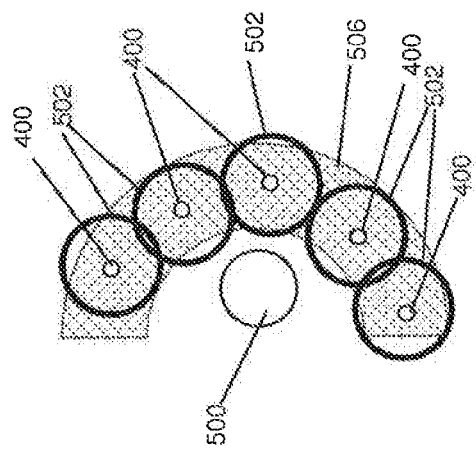
Figure 5C:
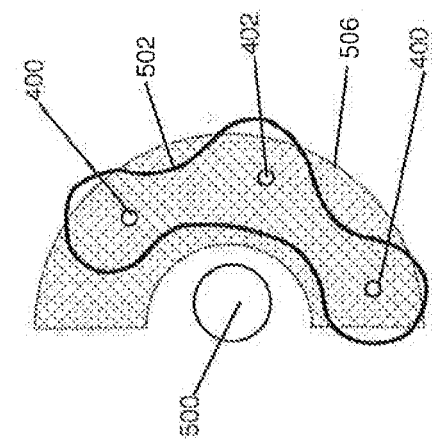
Figure 5D:
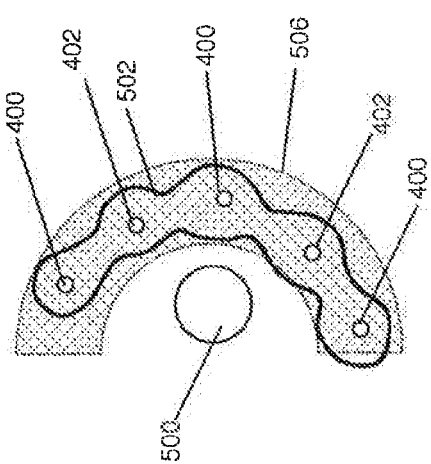

In another embodiment of this aspect of the present invention, as shown in FIG. 5B, three probes 400 may be inserted lateral to a sacral foramen 500, in the region of sacral neural crescent 506, such that the probes 400 are positioned substantially perpendicularly to the sacrum or generally upstanding relative to the sacrum. For example the shaft of the probes may be at an angle of between about 80.degree. to about 100.degree. relative to the circular face of foramen 500 (the surface of the sacrum), or in some alternate embodiments the angle between the probe shaft and the face of the foramen may be between about 60.degree. to about 120.degree. or, in other alternate embodiments between about 45.degree. to about 135.degree. relative to the circular face of the foramen 500. The probes may be operable in a monopolar configuration, whereby each probe 400 lies at the same electric potential such that current flows substantially between each probe 400 and a dispersive electrode such as a grounding pad. In other embodiments, an alternate number of probes may be used, and the invention is not limited in this regard. For example, as shown in FIG. 5D, five probes may be used, all of which may lie at the same electric potential.

As described above with respect to the first embodiment of a method aspect of the present invention, the step of inserting one or more probes adjacent one or more sacral foramina may comprise visualizing foramen 500 adjacent to a target site, for example using fluoroscopic imaging, penetrating into the tissue overlaying the sacrum using one or more rigid introducer tubes or other insertional means, and inserting the probes through the insertional means. In embodiments using multiple probes that are coupled, for example to a stage or other probe assembly, as described above, the step of visualization may be followed by a step of adjusting the positions of the probes relative to the assembly prior to insertion of the probes. As has been mentioned above, the relative spacing of the probes may be set so that no interference occurs between the probes during energy delivery. Thus, the probe(s) may be inserted substantially concurrently, for example by using a probe assembly to which the probes are coupled, or they may be inserted sequentially, for example one at a time. In alternate embodiments, a single probe may be used, wherein the probe is reinserted or otherwise repositioned at various locations, as described below, in order to create a desired lesion.

The probes may be inserted substantially perpendicularly to the circular face of the foramen, such that when visualizing the foramen using a fluoroscope or x-ray, visualization of the probes will be along the length of the probe shaft, in a "gun barrel" view; this angle of approach may potentially minimize tissue damage during insertion as a minimal amount of tissue will need to be penetrated, and may also aid in proper positioning of the probes. Penetration into the tissue may also be facilitated by the use of sharp or pointed probes, by the use of a stylet, by the insertion of a guide wire or by any other insertional means (i.e. means for insertion) and the invention is not limited in this regard. It should also be noted that the introducer(s) or other insertional means may be electrically and/or thermally insulated and they may be bent or straight. Furthermore, the length and diameter of the insertional means are not limited to specific values and any suitably sized introducer may be used. For clarity, the term introducer will be used throughout this specification and is intended to encompass any means for insertion that may facilitate entry of a probe into a specific site within the body of a patient. In such embodiments, these introducers may be capable of penetrating into a patient's body as well as penetrating through one or more of the ligaments of the sacroiliac region. In alternate embodiments, a probe may be positioned at the appropriate location within a patient's body without using any additional means to facilitate insertion.

Thus, in one embodiment of this aspect of the present invention, and with reference again to FIG. 5B, a method for treating SIJS may be practiced as follows: a patient is made to lie prone on an operating table or similar structure, and local anesthetic is provided in the vicinity of the sacrum. Prior to the insertion of probe(s) or introducer(s), fluoroscopic imaging or other means may be used to visualize a patient's sacroiliac region in order to ascertain a desired approach for inserting the device(s) into the desired tissue. This may be particularly advantageous with respect to SIJS treatment procedures because the anatomical structures involved may vary significantly from patient to patient. In this embodiment, following visualization to align the plane of visualization and foramen 500 adjacent the treatment site, the probes are inserted radially away from, for example lateral, caudal or cephalad to, the lateral edge of a foramen, for example about 8 to about 12 mm, for example about 10 mm, from the lateral edge. These positions may or may not lie within the sacral neural crescent. Probes 400 should be placed at the 2 o'clock, 4 o'clock and 6 o'clock positions radially away from the lateral edge of a foramen when the foramen is viewed as a clock face. Alternatively, 2 probes 400 may be used and they may be placed at, for example, the 3 o'clock and 5 o'clock positions. In other embodiments, other numbers of probes may be used, and they may be at various positions around the foramen, and the invention is not limited in this regard.

In one embodiment of this aspect of the present invention, three introducers are inserted into a patient's body from an approach that may be substantially perpendicular to the surface of the target treatment site adjacent the foramen, such that a distal end of each introducer is positioned proximate to or adjacent the lateral edge of sacral foramen 500, or the sacral neural crescent 506. In some embodiments, the distal ends of the introducers and/or probes are positioned substantially superficial to the sacral bony surface, such that, in particular embodiments, there are no ligaments or other connective tissue between the distal end and the sacrum. In further embodiments, the distal ends of the introducers and/or the probes may be placed about 2 to about 6 mm away from the surface of the sacrum, for example about 4 mm away from the surface. For example, an introducer apparatus may be about 2 to about 6 mm longer than a probe such that, when a distal end of the introducer is placed adjacent to the surface of the sacrum, the distal end of a probe disposed within the introducer may be located about 2 to about 6 mm away from the surface. In other embodiments, various angles of approach and sites of entry may be used. Depending on the site of entry and the angle of approach that are chosen, the introducer may be either bent or straight. A bent introducer may take several forms and the invention is not limited in this regard. For example, it may be bent along a substantial portion of its length or it may have a bent tip, wherein the rest of the introducer may be straight. At this point, the position of one or more introducers may be verified using fluoroscopic imaging (or other imaging modalities) or other means, after which the probes may be inserted through a bore or lumen of each introducer. The probes may be positioned at an angle such that the target treatment site is visualized straight down the shaft of the probes, and the probes may appear in cross-section, as shown in FIG. 5. It should be noted that, in those embodiments that comprise a stylet to facilitate positioning of the probe, the stylet may be disposed within an introducer and may be removed from the introducer prior to insertion of the probe.

As mentioned above, it may be advisable, at this stage, to ascertain the location of one or more of the probes with respect to any sensory and/or motor nerves that may be located close to the conductive regions of the probes by stimulating the neural tissue at one or more frequencies and determining the effect of said stimulation, as has been described. The stimulation of neural tissue may be performed in a monopolar manner, wherein energy passes between one or more probes and a dispersive return electrode. Using this step, it can be determined whether a target nerve or nerves has a function that would contraindicate its ablation or functional alteration. In this embodiment, the lack of a contraindication would lead to the step of delivering energy, whereas the presence of a contraindication would lead back to the step of inserting a probe or probes, whereby the step of inserting a probe or probes comprises modifying the position of a probe or probes within the body. In alternate embodiments, no stimulation is performed and a user may rely on his or her knowledge to determine whether or not to proceed with the treatment procedure.

At this point, energy may be delivered from energy source 206 via the probes to the target treatment site. Referring still to FIG. 5B, energy may be delivered in order to create a lesion lateral to foramen 500, such that the lesion may, in some embodiments, encompass at least one sacral nerve exiting foramen 500 and/or one or more lateral branches of the sacral nerve. For example, in embodiments utilizing monopolar RF, a substantially spherical lesion, for example an oblate or prolate spheroid, may form around each probe, which may result in a total effective lesion 504 as shown in FIG. 5B. A portion of lesion 504 may form due to conduction of energy through the tissue, rather than due to direct delivery of energy from probe 400. In some embodiments, the lesion may have a height of about 1 mm to about 15 mm, for example about 8 mm to about 10 mm, in order to account for variability in the location of the nerves to be treated. In some embodiments, the user may adjust a parameter of the treatment procedure in order to modify the height of the lesion, and thereby increase the size of the lesion, as described herein above. As will be described below, energy delivery to the probes may be substantially concurrent or it may be sequential, depending, for example, on the number of probes used, the energy source 206 and the preferences of the user.

Following the step of energy delivery, if one or more of the probes are steerable, the tips of one or more of the probes may be maneuvered to a second location and energy may again be delivered to ablate the neural tissue at the second location. This may be repeated as many times as the user feels is necessary. If no probes are steerable, the insertion and positioning steps may be repeated so that one or more of the probes is removed and reinserted to a second position, at which point energy may be delivered again at this location. For example, in some embodiments, only one probe may be used. In such embodiments, the probe may be placed at a first position adjacent to the foramen as indicated above, for example at the 4 o'clock position. After energy delivery has been completed at this position, probe 400 may be removed and reinserted into the 2 o'clock position and the energy delivery step may be repeated. Subsequently, the probe may be removed and reinserted into the 6 o'clock position and the energy delivery step may again be repeated. Alternatively, rather than being removed and reinserted, the probe may instead be repositioned while remaining within the patient's body. For example, a probe 400 may be inserted, in some embodiments with an introducer, at the 4 o'clock position, at which point energy may be delivered. Subsequently, the position of the same probe may be adjusted such that the distal tip lies substantially at the 2 o'clock position and energy delivery may be repeated. Similarly, the probe position may then be adjusted, for example without removing the probe from the patient's body, such that the distal tip lies substantially at the 6 o'clock position and energy may again be delivered. It should be evident that the specific order of the probe positions may be varied; for example, the probe may initially be placed at either the 2 o'clock or 6 o'clock positions and subsequent reinsertions may be at any of the other two positions. In some specific embodiments, for example when anesthetic is supplied to the target site, it may be desirable to position the probes in an order that accounts for the drift of the anesthetic. For example, if the anesthetic is expected to drift cranially, it may be beneficial to first place a probe at the 2 o'clock position and proceed caudally to the 4 o'clock and 6 o'clock positions. Once the user has determined that enough neural tissue has been ablated, the introducer and the probe may be removed from the body and the patient should be allowed to recover. It should be noted that this description is intended to be exemplary only and that other embodiments are envisioned as well. In addition, this invention is not intended to be limited by the number and type of probes used in this and other embodiments.

During the step of inserting the probe(s), the position of the probe(s) or introducer(s) may be visualized and/or monitored, for example by using fluoroscopy or other imaging modalities. If fluoroscopy is used, visualization may be improved by incorporating radio-opaque markers onto one or more of the probe(s) or introducer(s) and/or by injecting radiopaque dye into the patient's body. In some embodiments, radiopaque markers may be incorporated onto a distal region of the probe(s) in order to determine the distance that the probe(s) are extending out of the introducer(s). In addition, visual depth markers may be used to help determine the position of the probe(s) or introducer(s) within the body. Furthermore, positioning may be confirmed by measuring the impedance of tissue at the location of the probe(s) or introducer(s). In some embodiments, insertion and positioning are beneficially aided by the stimulation of tissue. Stimulation energy is delivered to the target site via one or more probes at a frequency sufficient to cause muscle contraction, nociceptive sensation, or other physiological response. In addition, some embodiments of the present invention may comprise one or more stylets having electrical connections such that the one or more stylets may be operatively connected to the energy source 206. In such embodiments, stimulation energy may be delivered to the target site via the one or more stylets prior to removal of the stylets and insertion of the probes. The effects of stimulation are sensed by one or more sensing means or, additionally or alternatively, by observation. In some embodiments, positioning may not be verified using these means and a user may rely in whole or in part on his knowledge of a patient's anatomy in order to accurately place the device(s).

Referring now to the step of delivering energy through the probe(s), this may be accomplished by providing an energy source 206, operable to deliver radiofrequency (RF) energy; connecting energy source 206 to the probe(s); and operating energy source 206 to deliver RF energy to the tissue through an energy delivery means, for example a conductive region associated with a distal region of the probe(s), such as an active tip or active electrode. In one embodiment, energy source 206 is operable to deliver sufficient energy to the tissue through the probe(s) so that the tissue may be ablated, as has been mentioned. Energy source 206 may be operable to be concurrently coupled to all of the probes used to deliver energy to the patient's body during the course of the treatment procedure. As mentioned above, in some embodiments, one or more probes may be 'on' (i.e. transmitting or receiving current) at a given point in time while other probes are 'off' (i.e. not transmitting or receiving current), while in other embodiments all probes may be transmitting or receiving current substantially concurrently.

Ablation of the dorsal sacral nerves exiting laterally from the sacral foramina by the creation of a lesion may prevent the transmission of pain sensations. In some embodiments, RF energy may be delivered in a series of amplitude or frequency modulated pulses, whereby tissue heating is inhibited by interrupting periods of energy delivery from one or more probes with relatively long periods in which no energy is delivered via the one or more probes. As has already been mentioned, in some embodiments the probes may be pulsed sequentially, such that while one probe is delivering energy another probe is not. This interrupted delivery would allow heat to dissipate further radially from the un-insulated tip without causing local coagulation (during the no energy delivery stage). Subsequent durations of the energy delivery stage would provide necessary heating of tissue and effectively created a virtual "cooled lesion", i.e. a larger lesion than may be achieved using an un-cooled probe and uninterrupted energy delivery. Furthermore, some methods of treatment involve delivering energy to achieve a different effect, for example, increasing collagen production, remodeling collagen, up-regulation of heat-shock proteins, alteration of enzymes, and alteration of nutrient supply. In further embodiments, a generator may not be used. In these embodiments, energy source 206 may take the form of a battery, in which case the entire apparatus (probe and energy source 206) may be hand-held/portable/modular, or any other energy source 206, and the invention is not limited in this regard. To summarize, any delivery of energy that may result in a treatment effect is intended to be included within the scope of this aspect of the present invention.

Regarding connecting energy source 206 to the probe(s), in some embodiments, energy source 206 may be releasably coupled to the probe(s). For example, this may be achieved by providing releasable electrical connectors 310 at or proximate to the proximal region of the probe(s) or at a proximal end of a cable or other connecting means coupled to the probe(s). In embodiments in which the probe(s) are cooled, the proximal region of the probe(s) may further comprise releasable connectors, such as Luer lock fittings for example, to couple one or more cooling means, such as peristaltic pumps and associated tubing, to the probe(s). In alternate embodiments, the probe(s) may be permanently coupled to the energy source 206 and/or the one or more cooling means.

In one embodiment of this aspect of the present invention, the method may further comprise a step of moving the probe(s) to another location within the tissue if the user so desires. The probe(s) may be moved before, during, or after the step of delivering energy, and may be moved one or more times. The step of moving the probes may comprise one or more of the following actions: applying a force to bend one or more of the probes within the tissue (wherein the probe may thus be described as a 'steerable' probe), moving one or more of the probes intact within the tissue, removing one or more of the probes intact from the tissue, reinserting one or more of the probes into the tissue and moving one or more parts of the probe (for example, extending or retracting a segmented probe telescopically) to move the position of one or more functional elements within the tissue.

In alternate embodiments of this aspect of the present invention, energy may be delivered in forms other than radiofrequency electrical energy, including but not limited to: other forms of electromagnetic energy, thermal energy, optical energy, mechanical energy and ultrasonic energy. Additionally, the step of delivering energy could involve the use of other energy delivery devices including, but not limited to: microwave probes, optical fibers, resistive heaters, and ultrasound emitters/transducers.

As was mentioned briefly above, the step of delivering energy to the tissue, may involve, in some embodiments, the use of apparatuses in which any of the one or more probes are actively or passively cooled. Cooling of probes can prevent the searing or coagulation of tissue directly adjacent to the probe(s) and can prevent the vaporization of liquid within the tissue. Cooling can also be used to increase the maximum lesion volume that can be formed in a given tissue. In one embodiment using three probes, as described above with reference to FIG. 4A, probe 402, having a relatively larger conductive region and serving as the effective return electrode for both probes 400, may have a high degree of cooling since it would normally tend to have the highest temperature, while probes 400 may have a relatively low degree of cooling in order to avoid tissue charring and popping adjacent the probes. The degree of cooling may be affected by, for example, the temperature of a fluid used to cool the probes and/or the flow rate of the fluid through the probes. In another embodiment, higher cooling may be supplied to probes at the 2 o'clock and 6 o'clock positions, with lower cooling being supplied to the probe at the 4 o'clock position. Alternatively, the degree of cooling may be substantially equivalent for all of the probes. In addition, the degree of cooling may be fixed or variable during the course of a treatment procedure for any of the probes.

In some embodiments, cooling may be shared between two or more probes, such that the cooling output of one probe is the cooling input of another. Such a configuration could beneficially allow cooling of multiple probes without requiring an individual cooling supply, such as a pump, for each probe. For example, in an embodiment using 3 probes, such as that shown in FIG. 4A whereby energy is delivered between two probes 400 and a single probe 402, the pair of probes 400 may share a cooling source, and the single probe 402 may have a separate cooling source. Using cooling in conjunction with monopolar energy delivery may allow for more precise control of lesion size than may be possible when delivering energy in a bipolar configuration. This may be due to the fact that the cooling of each monopolar probe may be independently controlled while the cooling of each of the bipolar probes may be dependent upon the other bipolar probe in order to maintain the effective flow of current between the probes. In addition, cooling may be used to project a lesion away from the probe(s) as has been mentioned above.

In addition to optionally measuring impedance, as in the embodiment described above, some embodiments further comprise an additional step of measuring the temperature of tissue at least at one location. This may be desirable so as to ensure that a given region of tissue is not exceeding a certain temperature. For example, in some embodiments it may be desirable to maintain the temperature of tissue at or below a temperature required for neural ablation, for example about 42.degree. C. In some embodiments, a temperature monitoring means may be located on or within a distal region of the one or more probes and the temperature of tissue located proximate to the distal region(s) of one or more of the probe(s) may be monitored using the temperature monitoring means. Temperature measurements may be averaged or otherwise combined from two or more probes or each probe may be monitored independently. Alternatively or in addition, a temperature monitoring means may be located at a different location on the one or more probe(s) to monitor the temperature of a region of tissue located some distance away from the distal region(s) of the probe(s). Furthermore, one or more separate temperature monitoring means may be inserted into the patient's body in order to monitor the temperature of one or more specific regions of tissue. The temperature monitoring means may take the form of thermocouples, thermistors, optical thermal sensors or any other temperature sensing or monitoring means and the invention is not limited in this regard. The temperature monitoring means may be connected directly to the energy source 206 (e.g. the RF generator) or to a controller associated with energy source 206. Alternatively, the temperature monitoring means may be monitored by an independent temperature monitoring device. These embodiments are intended to be exemplary only and are not intended to limit the present invention in any way.

As a feature of this aspect of the present invention, embodiments of this method may further comprise one or more steps of modifying a treatment procedure in response to one or more measured parameters. These measured parameters may include, but are not limited to, temperature, position of the probe(s) or impedance. For example, if a temperature measurement is determined to be outside of a desired range, a treatment procedure may be modified by, for example, altering the amount of energy delivered by energy source 206, modifying or modulating the one or more cooling means in some way, or terminating the procedure. In one embodiment of the present invention described above (and shown in FIGS. 4A and 5A), a temperature measurement from a probe 402 having a larger conductive region 306 may be used to control energy delivery while temperature measurements from probes 400 may be used to ensure patient safety. As another example, the amount of energy delivered by the energy source 206 may be modified based on the position of the one or more probes (for example, depending on the distance between a probe and the target treatment site or on the distance between the probes themselves when more than one probe is used). In such embodiments, wherein a treatment procedure may be modified, a feedback apparatus may be associated with or incorporated into the energy source so that any modification of a treatment procedure in response to a measured parameter may occur automatically, without any input from a user. In other embodiments, there may not be an automatic feedback apparatus in place, in which case a user may manually modify a treatment procedure in response to a measured parameter. In addition to modifying a treatment procedure based on measured parameters, this invention also provides for a step of determining the initial parameters to be used in a treatment procedure (for example, the initial maximum power level or tissue temperature, temperature ramp rate, etc.) using information that is known about the particular tissue to be treated. For example, if pre-treatment testing reveals specific information about the sacrum of a particular patient (this information may include, but is not limited to: the topology of the sacrum, location of specific nerves, etc.), that information may be used to decide on what parameters to use initially for the treatment procedure.

In some embodiments of this aspect of the present invention, the step of performing a treatment operation in order to reduce pain may comprise the addition or removal of material to or from the body. Material that may be added to the region of tissue being treated includes, but is not limited to, alcohol, chemical lysing agents, pharmaceutical agents or contrast media. Material that may be removed from the region of tissue being treated includes, but is not limited to, ligamentous tissue or other connective tissue. The removal of material may be accomplished through various means, which can include aspiration, vaporization and/or mechanical conveyance. Furthermore, the steps of addition and removal of material can be performed concurrently, for example by irrigating the tissue with a liquid medium while aspirating the liquid effluent. The addition or removal of material may also be combined with the delivery of energy, as has described above, wherein the delivery of energy and the addition or removal of material may occur concurrently or sequentially.

In an alternate embodiment of a method aspect of the present invention, probes may be inserted to the target site using different approaches. For example, it may be beneficial to insert the probes at a different angle with respect to the surface of patient's body. In one alternate embodiment, for example when using the probes in a bipolar configuration, it may be useful to follow a 'leapfrog' approach, wherein the probes are inserted to initial locations and a lesion is created between the probes. Once at least one lesion is created, one probe is repositioned with respect to a second probe, for example more substantially cranially along the sacrum lateral to the posterior foramen, and another lesion is created. Following this, the second probe is repositioned so as to be located on the other side of the first probe, even more substantially cranially along the sacrum, and so on. This method can also be practiced by using a multiplicity of probes and leaving each probe in place. In other words, once a probe is in place it may remain there and further probes may be inserted in order to achieve this 'leapfrog' lesioning approach. In other embodiments, both bipolar and monopolar configurations may be used in conjunction with various other approaches.

Although embodiments of the method aspect of the present invention has been described with respect to one specific application, i.e. treatment of SIJS, it should be evident that the apparatus and method disclosed herein may be used to treat various other conditions at various other treatment sites within a patient's body. As such, the embodiments of the various aspects of the invention described above are intended to be exemplary only. The scope of the invention is therefore intended to be limited solely by the scope of the appended claims.

It is appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating at least one target site in a sacroiliac region of a patient's body by delivering energy, the sacroiliac region including a sacrum having a posterior surface and a plurality of foramina extending therethrough, and a sacral neural crescent adjacent the foramina, the method comprising:
   inserting a plurality of probes into the sacroiliac region of a patient's body;
   positioning each of the plurality of probes with respect to a face of one of the foramina such that an angle between each of the plurality of probes and the face of one of the foramina ranges from 45° to 135°, each of the plurality of probes being inserted so that energy is delivered to at least one of 2 o'clock, 4 o'clock and 6 o'clock positions lateral to the face of one of the foramina, or at least one of 10 o'clock, 8 o'clock and 6 o'clock positions lateral to the face of one of the foramina, when one of the foramina is viewed as a clock face with 12 o'clock in the cranial direction;
   delivering energy from an energy source through each of the plurality of probes to the at least one target site in a bipolar configuration, and cooling at least one probe of the plurality of probes, wherein the at least one cooled probe is positioned from 10 mm to 26 mm from an adjacent probe of the plurality of probes.

2. The method of claim 1, wherein each of the plurality of probes are positioned with respect to the face of one of the foramina such that an angle between each of the plurality of probes and the face of one of the foramina ranges from 60° to 120°.

3. The method of claim 2, wherein the angle ranges between 80° to 100° from the face of one of the foramina.

4. The method of claim 1, further comprising inserting at least one of the one or more probes such that at least a portion of the at least one target site is distal to the distal end of the at least one probe.

5. The method of claim 1, wherein the at least one target site is located at least 1 cm lateral to the face of one of the foramina.

6. The method of claim 1, further comprising positioning at least one of each of the plurality probes such that it is perpendicular to the sacrum.

7. The method of claim 1, further comprising:
repositioning at least one of each of the plurality probes to a repositioned site; and
delivering the energy from the energy source through the at least one of each of the plurality probes at the repositioned site.

8. The method of claim 1, further comprising forming a lesion in at least a portion of the at least one target site via the delivered energy.

9. The method of claim 8, further comprising adjusting a parameter of a treatment procedure, wherein a size of the lesion is increased.

10. The method of claim 9, wherein adjusting the parameter of the treatment procedure comprises repositioning at least one of each of the plurality probes to alter a distance between each of the plurality probes and the at least one target site.

11. The method of claim 9, wherein adjusting the parameter of the treatment procedure comprises adjusting a length of an electrically exposed conductive region of at least one of each of the plurality probes.

12. The method of claim 9, wherein adjusting the parameter of the treatment procedure comprises modifying an amount of cooling supplied to at least one of each of the plurality probes.

13. The method of claim 1, wherein each probe of the plurality of probes is positioned at least 10 mm from each of the other probes of the plurality of probes.

14. The method of claim 1, wherein the at least one cooled probe is positioned from 15 mm to 26 mm from an adjacent probe of the plurality of probes.

* * * * *